(12) United States Patent
Damadian et al.

(10) Patent No.: US 8,055,325 B1
(45) Date of Patent: Nov. 8, 2011

(54) SEATED PATIENT SUPPORT AND USE THEREOF IN MAGNETIC RESONANCE IMAGING

(75) Inventors: Jevan Damadian, New York, NY (US); William H. Wahl, Smithtown, NY (US)

(73) Assignee: Fonar Corporation, Melville, NY (US)

(*) Notice: Subject to any disclaimer, the term of this patent is extended or adjusted under 35 U.S.C. 154(b) by 769 days.

(21) Appl. No.: 11/651,950

(22) Filed: Jan. 10, 2007

Related U.S. Application Data

(60) Provisional application No. 60/757,662, filed on Jan. 10, 2006.

(51) Int. Cl.
*A61B 5/05* (2006.01)

(52) U.S. Cl. ............. 600/421; 600/410; 600/415; 5/601

(58) Field of Classification Search .................. 600/415, 600/410, 421; 5/601
See application file for complete search history.

(56) References Cited

U.S. PATENT DOCUMENTS

| | | |
|---|---|---|
| 1,629,718 A | 5/1927 | Lockard |
| 4,534,358 A | 8/1985 | Young |
| D283,858 S | 5/1986 | Opsvik et al. |
| 4,771,785 A | 9/1988 | Duer |
| 4,824,302 A | 4/1989 | Schultheis et al. |
| 5,008,624 A | 4/1991 | Yoshida et al. |
| 5,018,918 A | 5/1991 | Jacobs et al. |
| 5,042,487 A | 8/1991 | Marquardt |
| 5,153,546 A | 10/1992 | Laskaris |
| 5,155,758 A | 10/1992 | Vogl |
| 5,305,365 A | 4/1994 | Coe |
| 5,349,956 A | 9/1994 | Bonutti |
| 5,379,768 A | 1/1995 | Smalen et al. |
| 5,386,447 A | 1/1995 | Siczek |
| 5,436,607 A | 7/1995 | Chari et al. |
| 5,520,181 A | 5/1996 | Kreidler et al. |
| 5,640,958 A | 6/1997 | Bonutti |
| 5,680,861 A | 10/1997 | Rohling |
| 5,735,278 A | 4/1998 | Hoult et al. |
| 5,743,264 A | 4/1998 | Bonutti |
| 5,779,637 A | 7/1998 | Palkovich et al. |
| D417,085 S | 11/1999 | Kanwetz, II |
| 5,983,424 A | 11/1999 | Naslund et al. |
| 6,212,251 B1 | 4/2001 | Tomura et al. |
| 6,246,239 B1 | 6/2001 | Krogmann et al. |
| 6,385,481 B2 | 5/2002 | Nose et al. |
| 6,404,202 B1 | 6/2002 | Damadian et al. |
| 6,414,490 B1 | 7/2002 | Damadian et al. |
| 6,424,854 B2 | 7/2002 | Hayashi et al. |
| 6,456,075 B1 | 9/2002 | Damadian et al. |
| 6,504,371 B1 | 1/2003 | Damadian et al. |
| 6,618,613 B1 * | 9/2003 | Shukla et al. .................. 600/425 |
| 6,776,527 B1 | 8/2004 | Tybinkowski et al. |
| 7,239,906 B1 | 7/2007 | Green et al. |
| 2001/0007588 A1 | 7/2001 | Iizuka |
| 2003/0160497 A1 * | 8/2003 | Darr .............................. 297/468 |
| 2003/0204136 A1 | 10/2003 | Green et al. |
| 2004/0030241 A1 | 2/2004 | Green et al. |
| 2004/0220467 A1 | 11/2004 | Bonutti |
| 2005/0187459 A1 * | 8/2005 | Trequattrini et al. .......... 600/415 |

* cited by examiner

*Primary Examiner* — Tse Chen
*Assistant Examiner* — Jason Ip
(74) *Attorney, Agent, or Firm* — Lerner, David, Littenberg, Krumholz & Mentlik, LLP

(57) ABSTRACT

A system for magnetic resonance imaging. The system comprises a magnetic resonance imaging apparatus having a pair of opposed elements spaced apart along a horizontal pole axis defining a patient-receiving space there between, a patient support apparatus having a rest member extending parallel to the horizontal pole axis, and a support arm connected to the patient support device and rest member, the support arm being operable to adjust the height of the rest member in a direction substantially perpendicular to the horizontal pole axis.

13 Claims, 10 Drawing Sheets

SEATED PATIENT SUPPORT AND USE THEREOF IN MAGNETIC RESONANCE IMAGING

CROSS-REFERENCE TO RELATED APPLICATIONS

This application claims the benefit of the filing date of U.S. Provisional Patent Application No. 60/757,662, filed Jan. 10, 2006, the disclosure of which is hereby incorporated herein by reference.

BACKGROUND OF THE INVENTION

The present invention relates to magnetic resonance imaging systems, apparatus and procedures and, in particular, to apparatus and procedures for improving safety when performing magnetic resonance imaging.

In magnetic resonance imaging, an object to be imaged as, for example, a body of a human subject, is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the precessing atomic nuclei to rotate or "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are the dominant factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Many conventional magnetic resonance imaging instruments require that a patient lie on a horizontal bed that is then advanced into a tubular bore within a super-conducting solenoidal magnet used to generate the static magnetic field. Other conventional MRI imaging instruments use a magnet having a ferromagnetic frame defining a patient-receiving space. Considerable effort has been devoted to the design of such magnets in a manner which provides a relatively open patient-receiving space, as opposed to the claustrophobic tubular bore of the conventional solenoidal magnet. However, in these instruments as well, it has been the common practice to provide the patient on a bed which remains horizontal throughout the procedure.

Advancement in magnetic resonance imaging has resulted in imaging apparatus that supports a patient in any position between a vertical position and a horizontal position. As described in greater detail in commonly assigned U.S. Pat. Nos. 6,414,490, and 6,677,753, a magnetic resonance imaging system can be provided with a patient support, such as a table, which can extend in a generally vertical direction so that the long axis of the patient is substantially vertical. For example, the patient may be in a standing posture, with his back, side or front leaning against a generally vertical patient support. Such a support may include a footrest projecting from the table at its lower end and the patient may stand on the footrest. In other arrangements, the support includes a seat projecting from the table so that the seat is in a horizontal plane when the table surface is vertical. In particularly preferred arrangements, the patient support can move relative to the magnet. For example, the patient support may be arranged to move vertically relative to the magnet so as to elevate a portion of the patient into the patient-receiving space of the magnet. Alternatively or additionally, the patient support may be arranged to tilt through a range of orientations between a generally horizontal orientation and a generally vertical orientation.

Where a patient is positioned on the patient support, the patient may sometimes require additional support members to prevent unwanted movement and injury. Unwanted movement can extend the time it takes to acquire images thereby reducing the throughput of the imaging apparatus. In addition, some patients may not be able to support themselves. This latter effect may sometimes occur with elderly patients. Furthermore, in some instances, additional support may be required because of the patient's condition. For example, a patient with a back condition may need support to maintain a desired imaging position, e.g., a substantially upright position.

In addition, in performing magnetic resonance imaging, an operator is usually not located next to the patient and usually needs to focus on the ancillary equipment, e.g., computers, etc., used to perform scanning. In such instances, mechanisms that may be used to provide additional safety and, for example, prevent a patient from leaving the patient receiving space without the aid of support personnel, are desirable.

Of utility then are methods and systems for preventing unwanted movement and enhancing the safety of a patient during magnetic resonance imaging.

SUMMARY OF THE INVENTION

In one aspect, the present invention comprises a system for performing magnetic resonance imaging. The system preferably comprises a magnetic resonance imaging apparatus having a pair of opposed elements spaced apart along a horizontal pole axis and defining a patient-receiving space there between and a patient support device positionable in the patient-receiving space, the patient support device being operable to support a patient in a sitting position. The system further desirably includes a patient support apparatus having a rest member extending parallel to the horizontal pole axis and a support arm connected to the patient support device and rest member, the support arm is desirably operable to adjust the height of the rest member in a direction substantially perpendicular to the horizontal pole axis.

In accordance with this aspect of the present invention, the patient support apparatus may further desirably comprise means for providing an indication that the patient is secured to the patient support.

Further in accordance with this aspect of the present invention, the patient support apparatus preferably comprises a seat that can be detachably mounted to the patient support device.

Further still in accordance with this aspect of the present invention, the seat may further include a frame supported on wheels and is adapted to transport a seated patient to the patient support device. It is further preferable that the patient support device is operable to position the chair in an imaging volume established between the opposed elements.

In addition, it also further desirable to have the patient support device detachably mounted to the seat.

Further still in accordance with this aspect of the present invention, the magnetic resonance imaging apparatus may comprise a superconducting magnet.

In another aspect, the present invention comprises a magnetic resonance imaging system. The system preferably comprises an apparatus having a frame supported by a plurality of wheels and a seat detachably mounted to the frame; a magnet resonance imaging magnet operable to generate a static horizontal magnetic field in a patient receiving space; and a patient receiving device that is positionable in the patient receiving space and that is adapted to receive and position the apparatus in the magnetic field generated by the magnet.

Further in accordance with this aspect of the present invention the apparatus may further comprise a support member that is mounted to the seat. The support member may include a support arm which is connected to a rest member.

Further in accordance with this aspect of the present invention, the support arm is preferably adjustable in a direction substantially perpendicular to the horizontal magnetic field. Further still, the magnet may further comprise a pair of poles separated along a horizontal pole axis.

In another aspect, the present invention comprises an apparatus for use in a magnetic resonance imaging system. The system preferably includes a patient support for positioning a patient within an imaging volume. The apparatus comprises a frame mounted onto wheels; and a seat detachably mounted to the frame. Further, the apparatus is preferably capable of engaging the patient support such that the seat can be detached from the frame of the apparatus and mounted onto the patient support.

Further in accordance with this aspect of the present invention, the frame of the apparatus may comprise a pair of support arms mounted to a base plate, the base plate being mounted onto a plurality of wheels.

In addition, the apparatus may further comprise a support member having mounted to the seat. Further still, the frame preferably has a width dimension that is larger than a width dimension of the patient receiving space.

In yet another aspect, the present invention may comprise a method. The method comprises: positioning a patient in a sitting position on a patient support apparatus, the patient support apparatus including a detachable seat; engaging the patient support apparatus to a patient support device of a magnetic resonance imaging system; detaching the seat from the patient support such that the seat is attached to the patient support device; positioning the patient in an imaging volume of the magnetic resonance imaging system; and eliciting magnetic resonance signals from a portion of the patient's anatomy.

DETAILED DESCRIPTION

Figure 1:
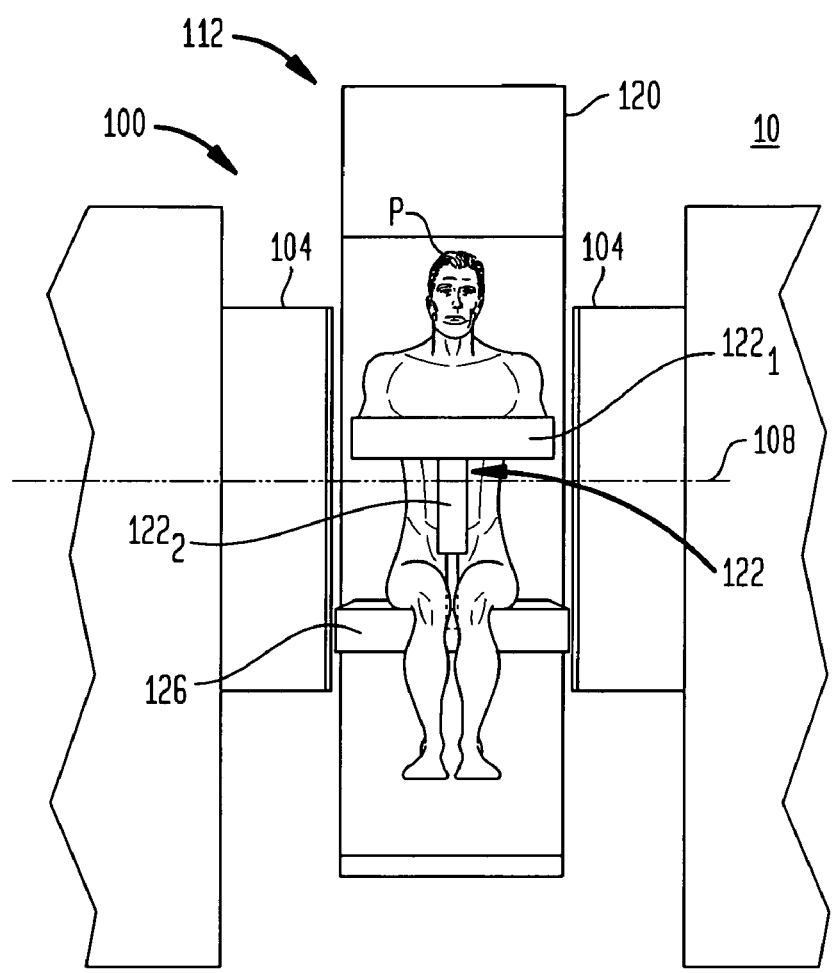
FIG. 1 illustrates a magnetic resonance imaging system in accordance with an aspect of the present invention.

FIG. 1 illustrates a schematic of a magnetic resonance imaging system in accordance with an aspect of the present invention. As shown, the system 10 includes an apparatus or magnet 100. The apparatus 100 preferably includes a pair of opposed elements 104 spaced apart along a horizontal field direction or polar axis 108. The space between the elements 104 is used as a patient receiving space 112. The system 10 also includes a patient support device or bed 120 which is positioned within the patient receiving space 112 and is used to support a patient P. The system 10 is marketed and sold by Fonar Corporation of Long Island, N.Y. and various aspects of the apparatus are described in U.S. Pat. No. 6,414,490, and U.S. application Ser. Nos. 10/438,353, 10/427,443, and 10/301,187, the disclosures of which are assigned to the assignee of the present application and hereby incorporated herein by reference. In accordance with the operational versatility of the system 10, the patient support and patient may be rotated about the horizontal axis between a fully upright vertical position, a horizontal position and even a reverse Trendelburg position. In addition, the patient may be raised or lowered. As the patient is positioned within the receiving space, it may be necessary to secure the patient to the support device or provide additional support assemblies or apparatus to prevent injury or unwanted movement.

The apparatus 100 may comprise a magnet that includes a frame and poles as described for example in the above mentioned patents and applications. In some embodiments the static fields may be generated using resistive electromagnetic coils that encircle the poles. The resistive electromagnetic coil may, however, be replaced by a conventional or high temperature superconducting coils. Superconducting coils are typically enclosed in vessels referred to as cryostats filled with a coolant such as liquid helium for conventional low temperature superconductors such as NbTi or $Nb_3Sn$ or, preferably, liquid nitrogen for high temperature superconductors. The coolant maintains the coils at a temperature low enough to provide superconductivity. The required temperature depends upon the composition of the superconducting material. The superconducting coils in their cryostats surround the poles in approximately the same position as the resistive coils.

As shown in FIG. 1, the patient P is preferably placed in a sitting position on the patient support device 120 and a patient support apparatus 122 is preferably attached to a seat 126 as shown. The patient support apparatus 122 preferably includes a rest member $122_1$ and a support arm $122_2$. The rest member and support arm are arranged so that the rest member extends parallel to the polar axis 108. With the patient support apparatus 122 positioned as shown in FIG. 1, patient P may place his forearms, chest or head on the rest member $122_1$ and use it for support during an imaging procedure. Alternatively, the patient support apparatus 122 may not be used to provide support. Instead, it may be used to insure that patient remains in the patient receiving space 112 during imaging.

This additional support is sometimes necessary to obtain the desired images and/or reduce the scanning time. For example, if a patient is experiencing pain or discomfort in their back or lumbar region, it may be desirable to have the patient lean forward and use the member 122 for support. This may result in a quicker diagnosis of the source of the patient's pain or discomfort. Furthermore, having the patient supported by the apparatus 122 also prevents unwanted movement, which also speeds up the imaging process.

Another advantage of having the patient support apparatus 122 is prevention of possible injury. For example, with elderly patients, there is sometimes a concern that the patient may fall asleep and lean forward during the imaging procedure. Without the restraint provided by the support apparatus 122, a patient may fall off the patient support 120. The provision of support apparatus 122 prevents these types of injury, thereby resulting in safer operation of the system. In that regard, and as shown FIG. 1, the support apparatus 122, is preferably adjusted to support or restrain a patient at chest level. In this way, as the patient leans forward their chest is brought to rest against the rest member $122_1$. Accordingly, as is discussed in further detail below, the outer surface of rest member $122_1$ is preferably covered with materials (e.g., cushions or foam) that comfortably support the patient.

Figure 2:
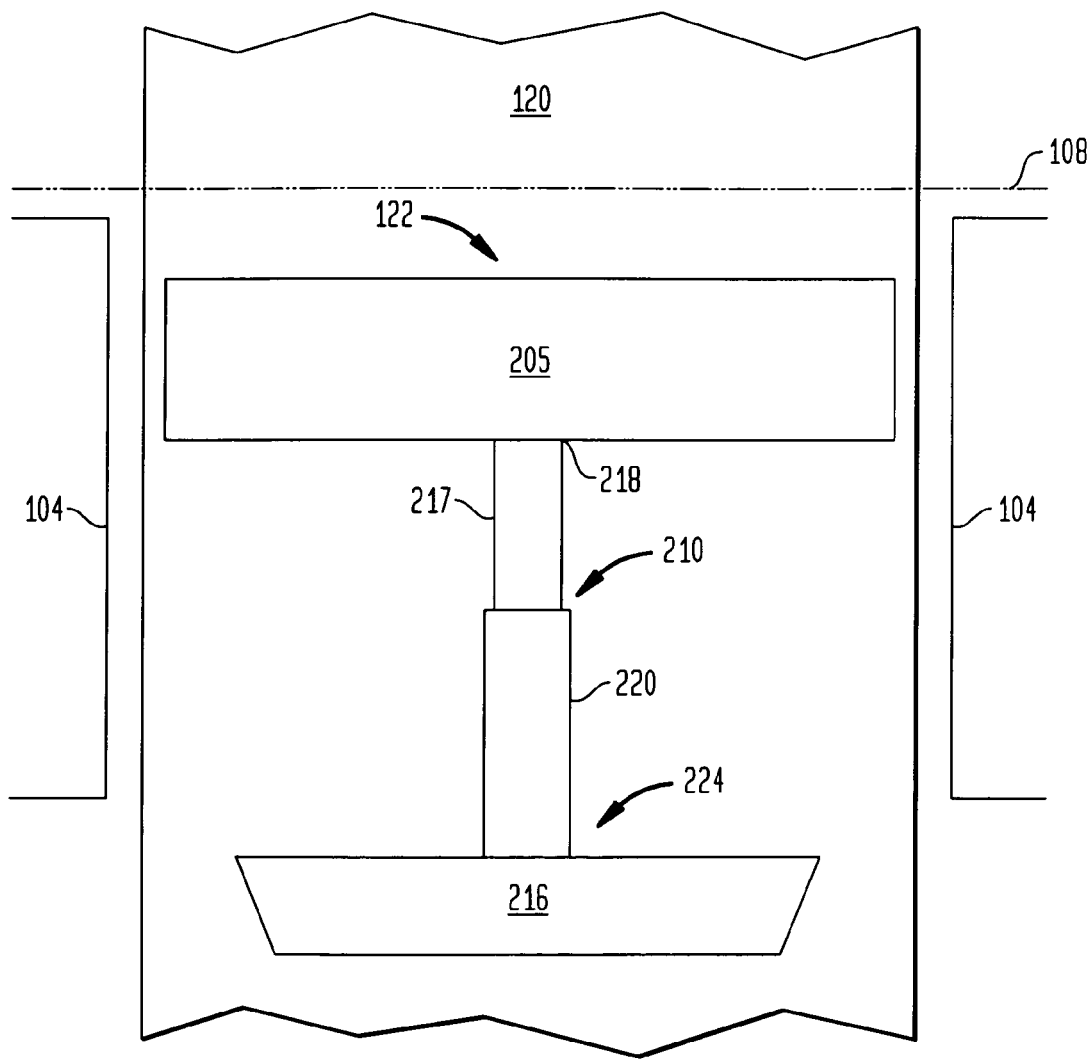
FIG. 2 is a front view of a patient support apparatus in accordance with an aspect of the present invention.

Turning now FIG. 2, there is shown a patient support apparatus in accordance with an aspect of the present invention. As shown in FIG. 2, the patient support apparatus 122 includes a rest member 205 that extends horizontally between the pole elements 104 and parallel to polar axis 108. The rest member 205 is connected to a support arm 210. The support arm 210 is connected to a seat 216, which projects from the patient support 120. The support arm 210 preferably comprises a columnar member 217 that is received within a sleeve 220. The columnar member 217 attaches to the rest member 205 at a proximal end 218, while the other end slides into the sleeve 220. The sleeve 220 includes a distal end 224 that connects to the seat 216. The sleeve 220 is preferably of a height that allows a patient unobstructed access to the seat 216. Alternatively, the support apparatus 122 may be designed to rotate out of the way of the patient thereby allowing access to the seat. Further, the support apparatus 122 and/or arm 210 may be designed to be detached from the seat.

Figure 3A:
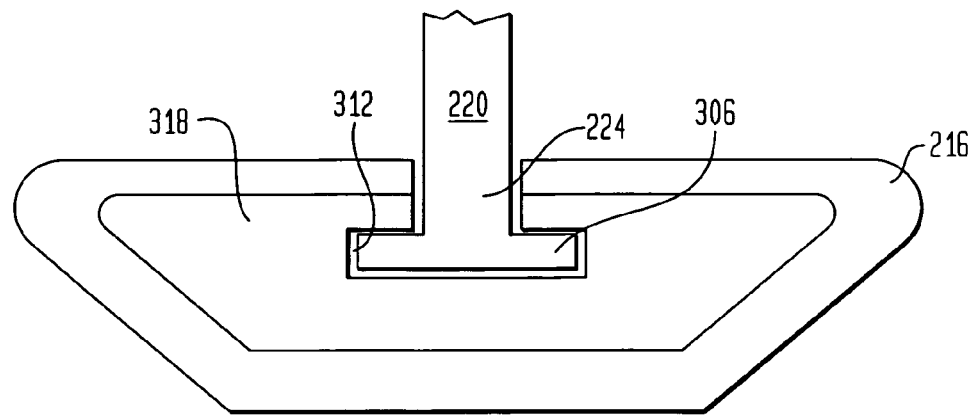
FIGS. 3A and 3B illustrate different views of a patient support apparatus in accordance with an aspect of the present invention.
Figure 3B:
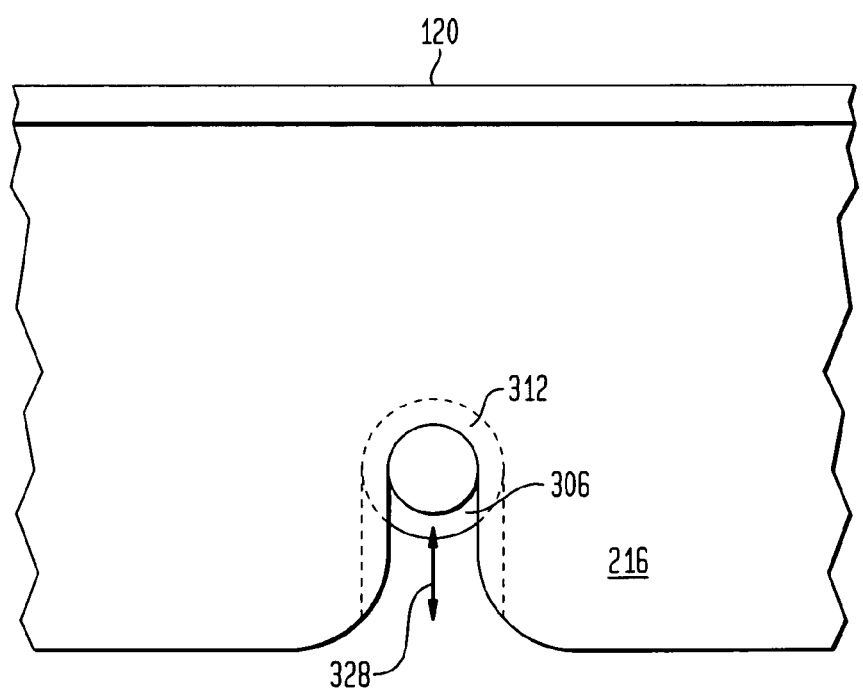

The distal end 224 may connect to the seat 216 in a number of ways. FIGS. 3A and 32 show one such possible connection. In particular, FIG. 3A is a front view of a cross-section of a seat in which the support arm slides into the seat. FIG. 3B is a top view of FIG. 3A. As these figures show, the distal end 224 may be formed so as to include a circular ledge 306. The ledge 306 is received into a slot 312 formed in a frame or base 318 of the seat 216. As seen in FIG. 3B, the distal end 224 and ledge 306 (and support arm 210) are insertable and removable into/from the seat 216 along direction 328. As previously discussed, the columnar member 217 and sleeve 220 comprise inter-mating circular cylindrical structures. Further, the distal end 224 and ledge 306 preferably form a unitary structure.

Figure 4A:
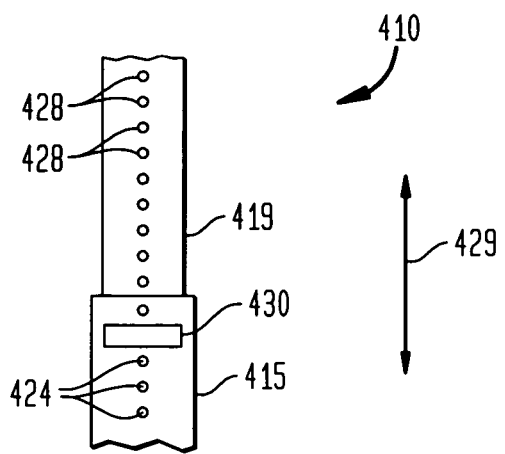
FIGS. 4A and 4B illustrate adjustment mechanisms for a patient support apparatus in accordance with an aspect of the present invention.
Figure 4B:
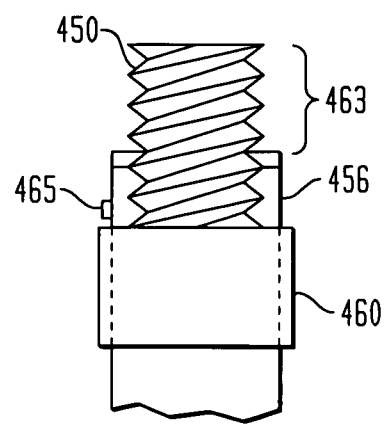

As discussed above (e.g., see FIG. 2), the rest member $122_1$ is preferably adjustable in a direction substantially perpendicular to the horizontal field direction 108. This allows for height adjustments to accommodate patients of different sizes. FIGS. 4A and 4B show exploded views of possible adjustable locking mechanisms in accordance with additional aspects of the present invention. In particular, FIG. 4A shows a support arm 410 that includes a sleeve 415, which is sized and shaped to receive an inner member 419. The sleeve 415 includes one or more holes 424 aligned in an axial direction 429. The sleeve holes 424 are aligned with one or more holes 428 on the inner member 419 when the sleeve 415 and inner member 419 are in an assembled condition. The mechanism also includes a locking pin 430 which includes a handle as shown. Preferably, each of holes 424 and 428 is aligned with rearward mating holes on the sleeve and inner member that allow the pin to be inserted through the sleeve 415 and mating member 419. In particular, the pin 430 is inserted through one of the holes 424 and one of the holes 428 to engage a respective mating hole. In this way, the pin 430 desirably locks the inner member 419 in place relative to the sleeve 415 to maintain a particular height adjustment.

Turning now to FIG. 4B, there is shown an alternative arrangement for adjusting the height of the rest member $122_1$. In this embodiment, a support arm includes an inner member 450, an outer member 456 and a collar 460. The inner member includes a threaded portion 463. The threaded portion 463 is engaged by mating threads (not shown) on the inner side wall of the collar 460. In that way, the collar can screw onto the inner member 450 to lock the assembly in place. The sleeve 456 may include a protrusion 465 that serves to stop the collar from moving up the sleeve 456 entirely on to the inner member 450. The sleeve 456 preferably includes an opening that is slightly wider that the inner member 450 so as to provide a snug fit without requiring an usual amount of force to slide the inner member 450 into and out of the sleeve 460.

Figure 5A:
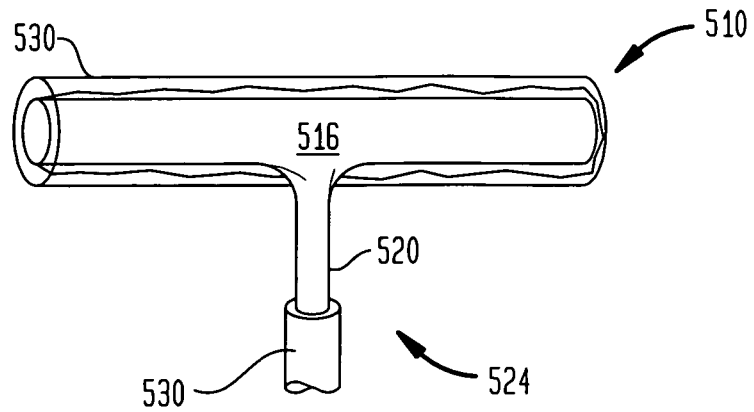
FIGS. 5A, 5B and 5C illustrate various views of a patient support apparatus in accordance with an aspect of the present invention.

Turning now to FIG. 5, there is shown possible arrangements for attaching a rest member to a support arm. FIG. 5A shows one embodiment in which a rest member 510 includes an inner core or frame 516. The core 516 and inner member 520 of a support arm 524 form a unitary structure. The rest member 510 also preferably includes an outer enclosure 530 around the core 516. The outer enclosure 530 preferably comprises a surface on which a patient may rest for support. The inner member 520 may be attached to the outer enclosure 530 as described above and including any of the above locking mechanisms.

Figure 5B:
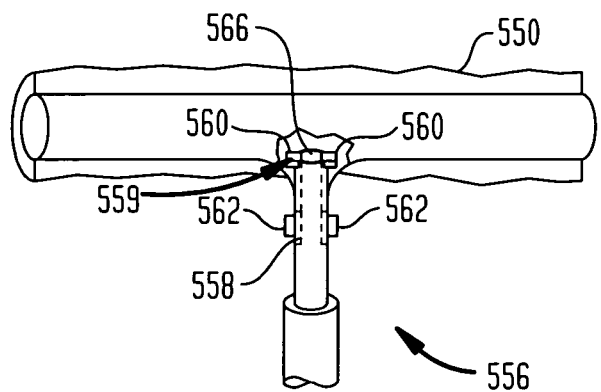

FIG. 5B shows an alternative embodiment of a rest member 550 and support arm 556 assembly. In this embodiment, the support arm 556 includes an inner member 558 that attaches to the rest member 550. As shown, the rest member 550 includes an opening 559 for receiving the inner member 558. The inner member includes detents 560 that extend outward from the inner member 558. The detents 560 are mounted through openings in the inner member 558. The detents are preferably releasably engageable through release buttons 562 mounted near the proximate end 566 of the inner member 558. When the release buttons 562 are pressed, the detents 560 retract into the housing of inner member 558. This allows the inner member 558 to be engaged and disengaged from and to the rest member 550, which includes one or slots within the walls defining opening 559.

Figure 5C:
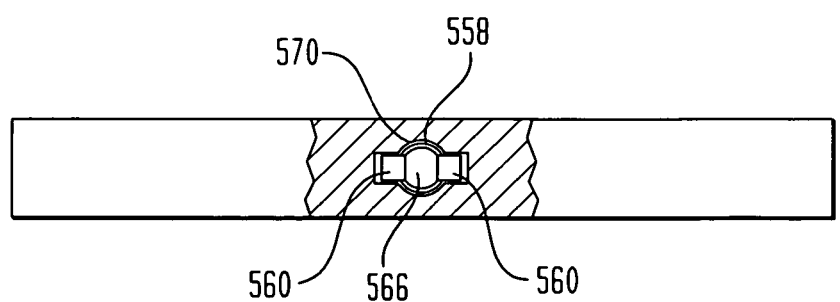

For example, as best seen in FIG. 5C, one or more openings 570 may be formed in the rest member 550. The openings 570 are preferably formed such that each detent 560 fits snugly into one of them in the engaged condition. When the buttons 562 are not pushed in, the detents 560 protrude away from the cylindrical axis 566 through openings in the inner member 558. The detents 560 extend down to the release buttons 562 such that as the release buttons are pushed in, the detents retract into the inner member 558. The detents and release buttons may be attached via various other means, including for example mechanical and/or electrical devices and their connections. Note also, the opening 570 may be made such that it extends circumferentially around the inner member and include stops that engage the detents in one or more locking positions.

As previously discussed, the rest member includes an outer portion that is preferably constructed from a cushiony material that provides a comfortable rest area for a patient. The cushiony material may comprise sponge or foam rubber or any other similar materials. The other structures that form the rest member and patient support member may be constructed from any number of materials including plastics or wood, as long as the materials are non-magnetic. For example, the patient support member from molded parts comprising G-10 fiberglass resin composite or high impact PVC, most preferably Type II high impact PVC. The support member may also be made from any other magnetically translucent (i.e., non-magnetic) and non-conductive material that do not interfere with obtaining images.

Figure 6:
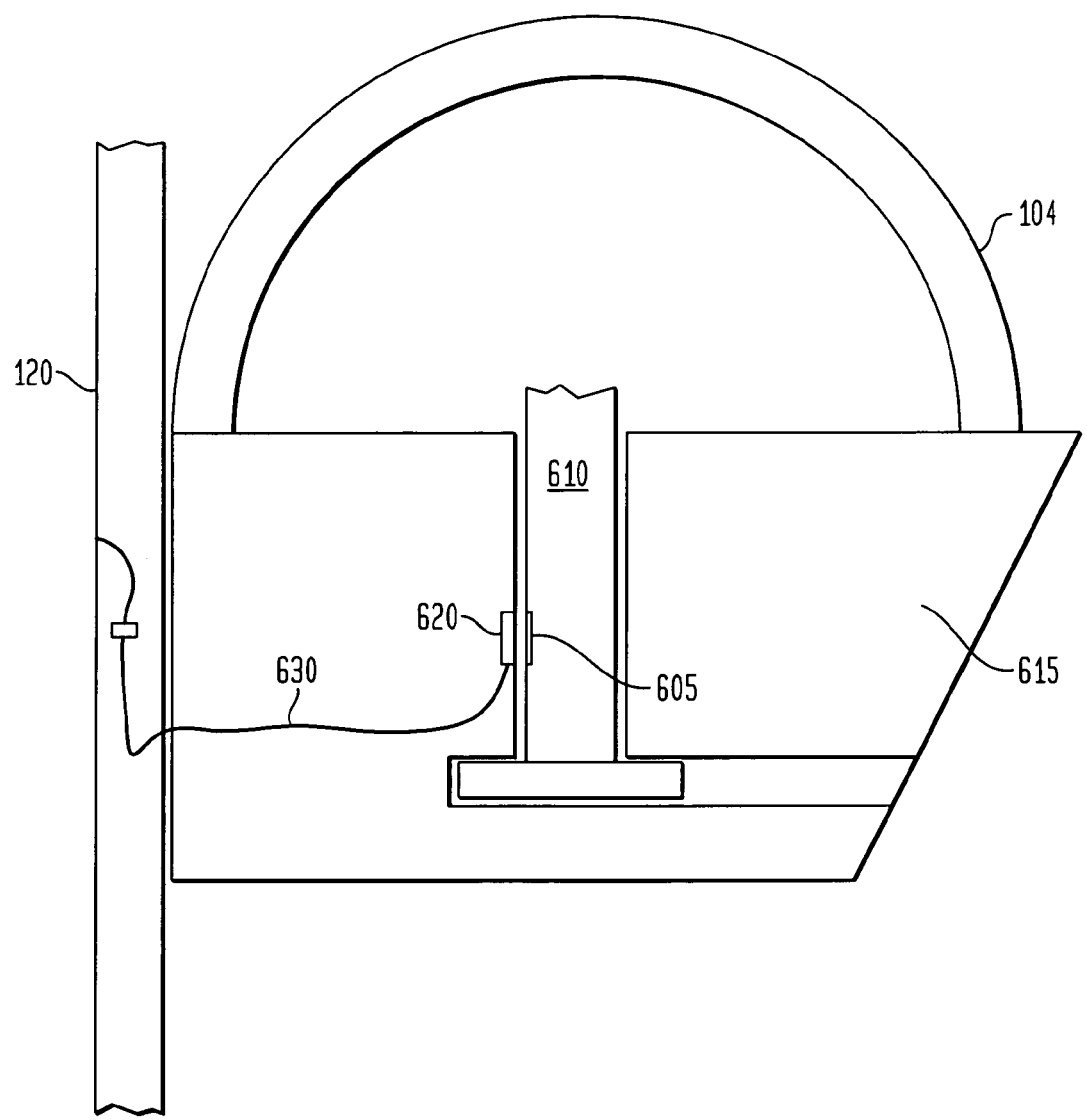
FIG. 6 depicts a side view of a patient support apparatus in accordance with an aspect of the present invention.

Turning now to FIG. 6, there is shown a system for detecting the presence of a patient support member during a scanning procedure in accordance with an additional aspect of the present invention. The system comprises a reflector 605 that forms a portion of an outer member or sleeve 610. The sleeve 610 forms parts of the patient support member, which is not shown in its entirety. When the patient support member is properly inserted in a seat 615, the reflector 605 is positioned next to a light emitting diode/optical detector assembly 620. The assembly 620 is connected via an optical cable 630 to ancillary equipment used to operate the magnet, including moving the patient support 120. The LED/detector assembly 620 transmits light to reflector 605. A portion of the light is reflected back to the detector assembly 620. The portion of the light that is detected is then used to provide an indication that the patient support member is in place. If the patient support member is removed, then the detector detects substantially less or no light at all which indicates the absence of the patient support member. In this way, the detector/LED and reflector assembly functions as a light switch.

Some care has to be taken in choosing the optical switch that provides an indication of whether a patient support member is properly engaged or affixed to a patient support device. In particular, some optical switches may include leads made of steel. The inclusion of even a minute amount of steel in the patient restraint member will affect the imaging process. More particularly, under most circumstances the presence of even particles of magnetic material (such as steel) within the imaging volume will prevent the acquisition of appropriate images.

In addition, although the detection system is described as using a optical detection, electrical circuits or other means may be used to detect the presence or absence of the patient support system as long as such system does not interfere with the imaging process, e.g., use magnetically translucent elements.

The optical or electrical detection circuit provided within the support apparatus 122 preferably provides feedback to an operator or technician at a console, kiosk or podium (not shown) with an indication of whether the restraint member is secured or not. Typically, the console is located outside the shielded room, and the kiosk or podium is located in the shielded room with the apparatus. In conjunction with the positioning and imaging of the patient, where the apparatus 122 provides an indication of an open circuit condition, the operation of the patient support device 120 and/or the operation of the magnet can be shut down or prevented. The indication or feedback may comprise audible or visual indication including, but not limited to, buzzers, lights or text. In contrast, where the restraint member provides a closed circuit condition, the operator is free to safely position the patient and perform imaging.

In some circumstances, the feedback provided through the support apparatus may be used to further indicate that a patient may be disoriented or fainted during the imaging process. This additional functionality may be implemented by use of a strain gauge in the support apparatus. These and other advantages of the present invention may be achieved not only in the apparatus depicted in FIG. 1, but in any imaging apparatus where patient safety is of consequence.

Figure 7:
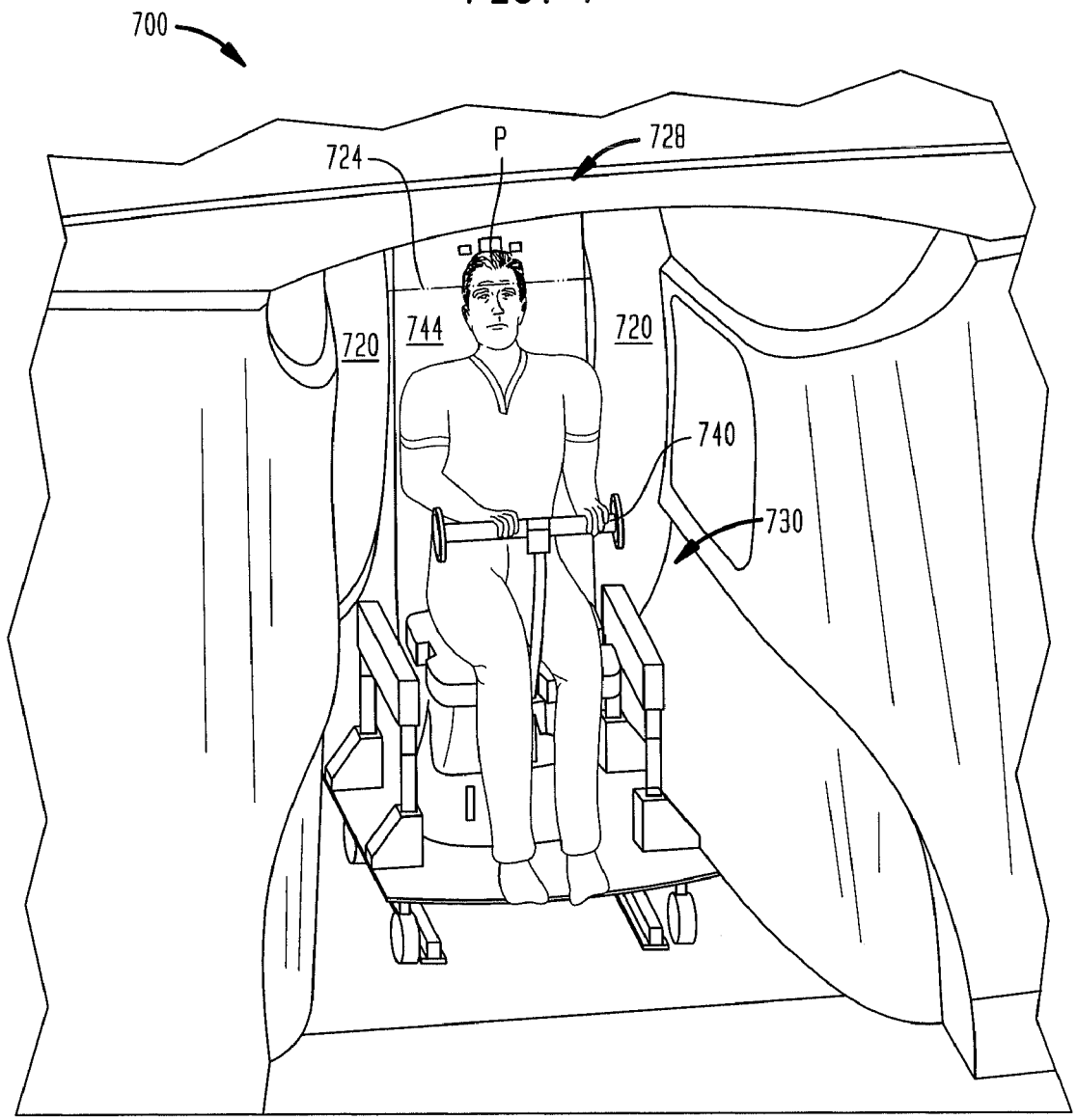
FIG. 7 depicts a magnetic resonance imaging system in accordance with an aspect of the present invention.

Turning now to FIG. 7, there is shown a magnetic resonance imaging system 700 in accordance with an aspect of the present invention. The system 700 includes a magnet that includes a pair of opposed elements 720 that are spaced apart along a horizontal field or pole axis 724. In FIG. 7, the opposed elements 720 are covered by a shroud and define a patient receiving space 728 therebetween. The system 700, like system 10, includes ancillary coils and other equipment for generating a static magnetic field and imposing gradients thereon to obtain magnetic resonance images of a patient P.

Figure 8:
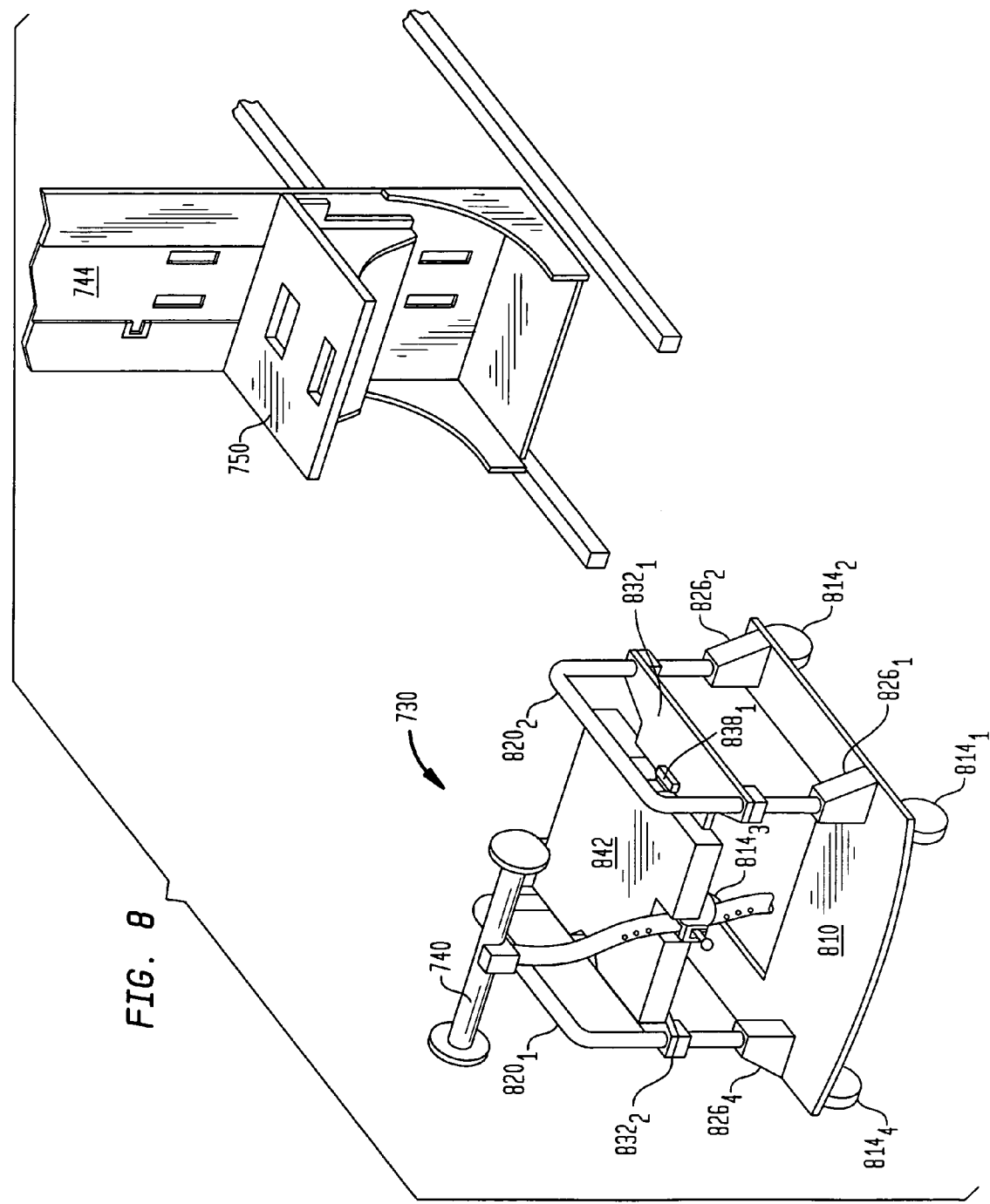
FIG. 8 depicts an exploded side view of the system of FIG. 7 in accordance with an aspect of the present invention.
Figure 9:
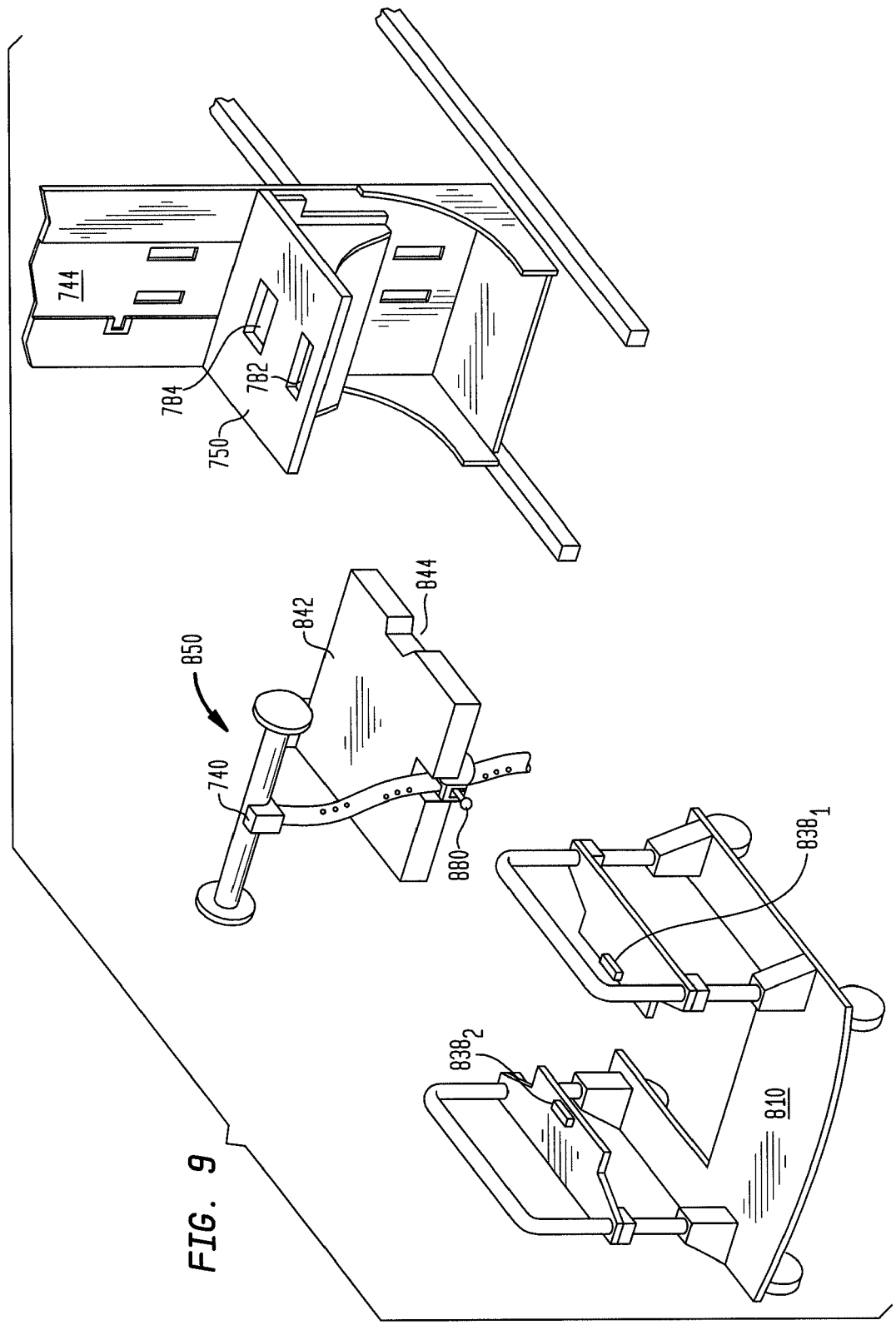
FIG. 9 depicts an exploded side view of a patient support apparatus and system in accordance with an aspect of the present invention.

As shown in FIG. 7, the patient P is seated on a patient support apparatus 730 that also includes a support member 740. As best seen in FIG. 8, the patient support apparatus 730 includes a base plate 810 that is supported on wheels 814. Each wheel preferably includes a locking tab or brake which can desirably hold the wheels in place. A pair of U-shaped arms 820 is mounted to the base plate 810 via fasteners. As shown, the open end of each arm 820 is mounted to the plate 810 via support blocks 826. In addition to providing a mounting connection, the support blocks 826 assist in stabilizing the arms 820 under a weight bearing condition. A pair of support members 832 is mounted to arms 820 proximate their closed end. In addition, the support members 832 may also be suitably mounted to the arms 820 approximately at the midpoint of the support arms, as preferably shown in FIG. 8. The support members, base plate and arms together form a frame for receiving a seat. In particular, each support member 832 includes a projection 838, which as best seen in FIG. 9, mates with a slot 844 on a seat 842. The seat is therefore removably mounted to the support members 832 as is also shown in FIG. 9.

As can be understood by reference to FIGS. 7, 8 and 9, the apparatus 730 desirably allows a patient seated thereon to be rolled into the patient receiving space 728, and secured to the patient receiving device or bed 744. In the preferred embodiment, a mounting member 750 is affixed to the patient receiving device 744 and operable to secure the apparatus 730 to device 744. With the apparatus secured to the device 744, imaging may take place as discussed above. In particular, the bed 744 may be translated further in the patient receiving 728 of magnet and raised so that the anatomy of interest can be positioned in the imaging volume established through elements 720.

The apparatus 730 is particularly advantageous where the patient is confined to a wheel chair. Aside from allowing for easier access to such patients, the apparatus 730 provides the additional benefit of being able to image such patients in an upright position by wheeling them into the patient receiving space. In addition, the apparatus avoids having to consider such issues as whether a patient's personal wheel chair is magnetically translucent. This enhances safety. Furthermore, as the apparatus is equipped with the support member 740, it also provides the additional benefits described above, which include preventing a patient from falling too far forward.

Figure 10:
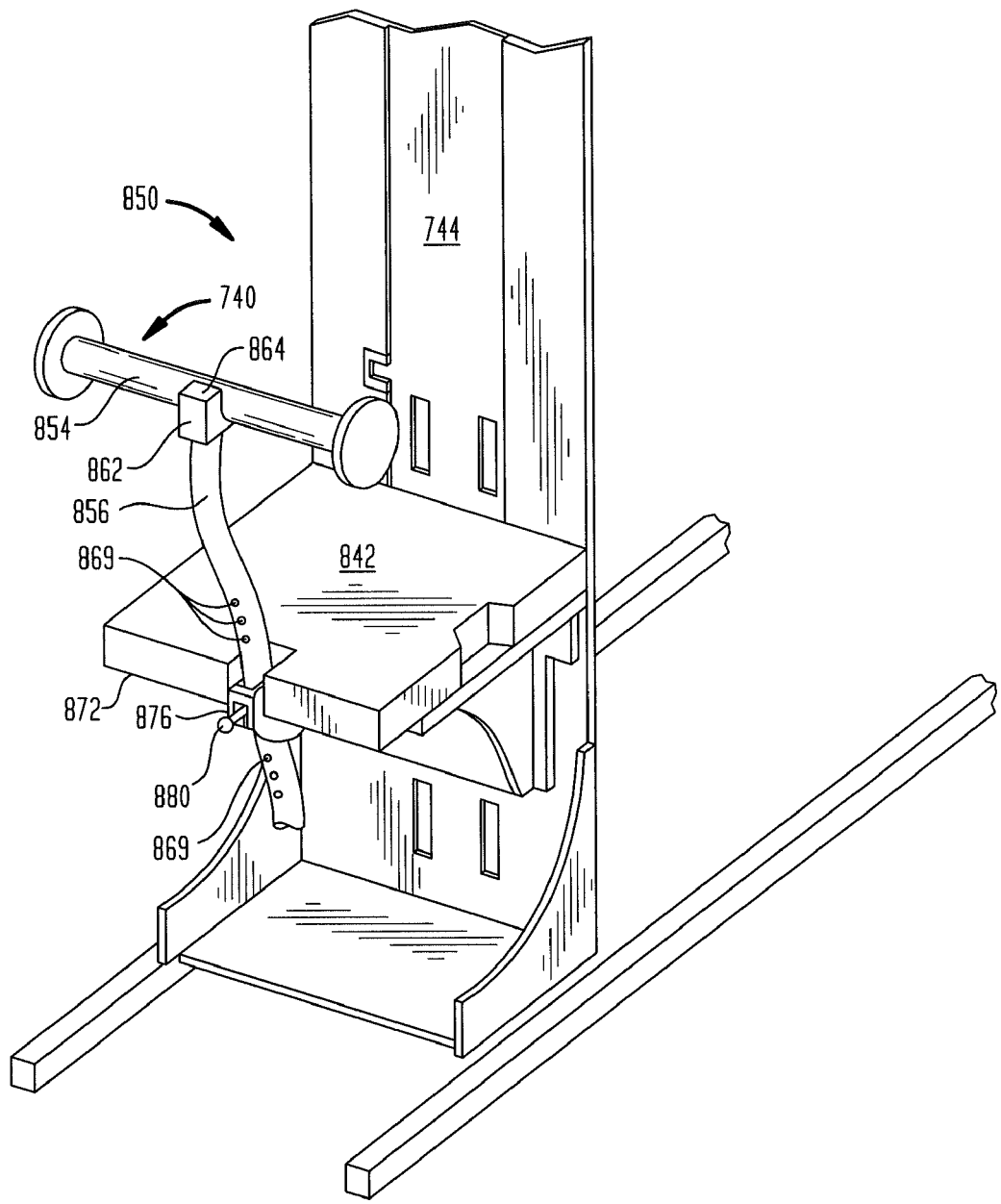
FIG. 10 depicts a patient support apparatus and system in accordance with an aspect of the present invention.

As discussed above, the seat 842 of the apparatus is preferably removably mounted to the support members 832. This provides an additional benefit as is best seen in FIG. 10. In particular, the seat 842 and support member 740 may be mounted to the patient receiving device 744, as shown.

With reference to FIGS. 9 and 10, the seat 842 and support member 740 form a support assembly 850. The support member 740 includes a rest member 854 that is connected to a support arm 856. The rest member 854 includes a bracket 862 at its midpoint that forms a slot 864 for receiving an end of the support arm 856. Support arm 856 includes a plurality of openings or detents 869 arranged along its longitudinal direction, which is substantially perpendicular to the magnet axis in the assembled condition. The openings 869 provide for adjustment of the support member along the longitudinal direction and may include matching openings on the back section of the arm facing the patient bed 744. Note, however, that in the preferred embodiment the holes or detents 869 do not extend through to the back section. In addition, the base 872 of the seat 842 includes a second bracket 876 into which the support arm 856 is mounted. The bracket 876 includes an opening through which a locking pin 880 is inserted. The pin 880 is preferably inserted and maintained in the openings on the support arm 856 so as to secure it in place. When an operator desires to adjust the height of the rest member 854 the pin 880 is removed and the arm 856 is adjusted accordingly. In that regard, the pin 880 is preferably spring loaded so as to maintain it in the locked position. Furthermore, in the preferred embodiment, the pin is inserted through the opening in the bracket 876 and engages the detents or openings 869. In accordance with this embodiment, the support member 740 can be removed from the seat 842 allowing a patient to be seated. Once the patient is seated, the support member 740 is inserted in the second bracket 876. Thereafter, the locking pin 880 is released to engage the detents or openings 869.

As is also shown in FIG. 9, the mounting member 750 includes at least openings 782, 784 for receiving the seat 842. In the preferred embodiment, the base 876 of the seat includes projections (not shown) that engage the openings 782, 784 and serve to further secure the seat in place on the mounting member 750.

The apparatus and seat discussed in FIGS. 7, 8, 9 and 10 may also be implemented to include either electrical or optical circuitry that provides feedback to the operator regarding the position of the apparatus, seat and patient in the patient receiving space. As discussed above, such circuitry allows an operator to avoid safety hazards associated with a patient leaving the patient receiving space or falling out the patient receiving space.

With reference to FIGS. 7-10, in operation a patient is positioned on the patient support apparatus 730 and wheeled into the area or room containing the magnet. In the preferred embodiment, the magnet includes a patient support device that may be translated outside the patient receiving space in the magnet to engage the apparatus 730. This advantageously allows the apparatus 730 to be designed to accommodate the size and load of a variety of patients. In particular, this allows the frame of the apparatus (e.g., support arms 820, base plate 810) to be wider than the width of the patient receiving space. This allows the apparatus to reliably and more comfortably support the load of larger and wider patients. In contrast, although a narrower support may be designed to fit in the receiving space, its design may be more costly to meet patient loading requirements (e.g., 500 pounds) and may not be as comfortable for large patients.

With the apparatus 730 and patient support engaged (e.g., see FIG. 7) via mounting member 750, the seat 842 and support member 740 may then be detached from the remainder of the apparatus. This results in the assembly shown in FIG. 10 (patient not shown). The patient support device 744 may then be translated back into the receiving space so that the patient can be properly positioned in the imaging volume. The patient may then be imaged. Once imaging is over the support device 744 may then be translated back outside the patient receiving space so that the seat 842 may be reassembled with the apparatus 730.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A system for performing magnetic resonance imaging, comprising:
   a magnetic resonance imaging apparatus having a pair of opposed elements spaced apart along a horizontal pole axis and defining a patient-receiving space there between;
   a patient support device positionable in the patient-receiving space, the patient support device being operable to support a patient in a sitting position and rotatable about the horizontal pole axis;
   a patient support apparatus having a rest member with an elongated portion that extends parallel to the horizontal pole axis and a support arm connected to the patient support device and rest member, the support arm being operable to adjust the height of the rest member in a direction substantially perpendicular to the horizontal pole axis, and
   wherein the patient support apparatus includes a frame supported on wheels and is configured to be rolled into the patient-receiving space and secured to the patient support device.

2. The system of claim 1, wherein the patient support apparatus includes means for providing an indication that the patient is secured to the patient support.

3. The system of claim 1, wherein the patient support apparatus comprises a seat that can be detachably mounted to the patient support device.

4. The system of claim 3, wherein the patient support device is operable to position a patient in an imaging volume established between the opposed elements.

5. The system of claim 3, wherein the patient support device is detachably mounted to the seat.

6. The system of claim 1, wherein the magnetic resonance imaging apparatus comprises a superconducting magnet.

7. The system of claim 1, wherein the magnetic resonance imaging apparatus comprises a resistive electromagnet.

8. A magnetic resonance imaging system, comprising:
   an apparatus having a frame supported by a plurality of wheels and a seat detachably mounted to the frame;
   a magnetic resonance imaging magnet operable to generate a static horizontal magnetic field in a patient-receiving space, the magnet including a pair of poles separated along a horizontal pole axis; and
   a patient-receiving device that is positionable in the patient-receiving space and that is configured to receive and position the apparatus in the magnetic field generated by the magnet, and wherein the apparatus further comprises, a support member having a support arm mounted to the seat, the support arm being connected to a rest member, the rest member including an elongated section that extends between the poles along the horizontal pole axis, wherein the apparatus includes the frame supported by the wheels and is configured to be rolled into the patient-receiving space and secured to the patient-receiving device.

9. The system of claim 8, wherein the support arm is adjustable in a direction substantially perpendicular to the horizontal magnetic field.

10. An apparatus for use in a magnetic resonance imaging system, the system including a patient support for positioning a patient within an imaging volume, and a pair of opposed elements spaced apart along a horizontal pole axis defining a patient-receiving space there between such that the patient support is rotatable within the patient-receiving space about the horizontal pole axis, the apparatus comprising:

a frame mounted onto wheels; and a seat detachably mounted to the frame, a support member having a first member and a second member, the first member being mounted to the seat and extending in an upright direction generally perpendicular to a sitting surface of the seat, the second member including an elongated portion extending along a direction perpendicular to the upright direction and being mounted to the first member, a detection system associated with the support member and the magnetic resonance imaging system for detecting when the support member is mounted to the seat, and wherein the frame mounted on wheels is configured to be rolled into the patient-receiving space and secured to the patient support.

11. The apparatus of claim 10, wherein the frame comprises a pair of support arms mounted to a base plate, the base plate being mounted to the wheels.

12. The apparatus of claim 10, wherein the support member is detachably mounted to the seat.

13. The apparatus of claim 10, wherein the second member is detachably mounted to the first member.

* * * * *